United States Patent [19]

LoPiano

[11] 4,211,223
[45] Jul. 8, 1980

[54] PULSED OXYGEN CHAMBER

[76] Inventor: Rocco W. LoPiano, 26 Journal Sq., Jersey City, N.J. 07306

[21] Appl. No.: 31,052

[22] Filed: Apr. 18, 1979

[51] Int. Cl.$^2$ .............................................. A61M 13/00
[52] U.S. Cl. ................................ 128/207.26; 128/299
[58] Field of Search ..................................... 128/38–40, 128/60, 64, 297, 298, 299, 184, 204, 30, 30.2

[56] References Cited

U.S. PATENT DOCUMENTS

| | | | |
|---|---|---|---|
| 1,172,662 | 2/1916 | Armbruster | 128/298 |
| 2,227,847 | 1/1941 | Schoolman | 128/299 |
| 2,354,397 | 7/1944 | Miller | 128/30.2 |
| 2,480,980 | 9/1949 | Terhaar | 128/30.2 |
| 2,825,327 | 3/1958 | Tunnicliffe | 128/30.2 |
| 3,744,491 | 7/1973 | Fischer | 128/184 |

*Primary Examiner*—Lawrence W. Trapp
*Attorney, Agent, or Firm*—DeLio and Montgomery

[57] ABSTRACT

A treatment chamber for a portion of a human body specially adapted for use with a pulsed or hyperbaric oxygen supply, the chamber comprising upper and lower sections adapted to be sealingly clamped together and provided at both ends with demountable annular sleeves fitting sealingly against the adjacent body surfaces, such as thighs and midriff, respectively.

7 Claims, 5 Drawing Figures

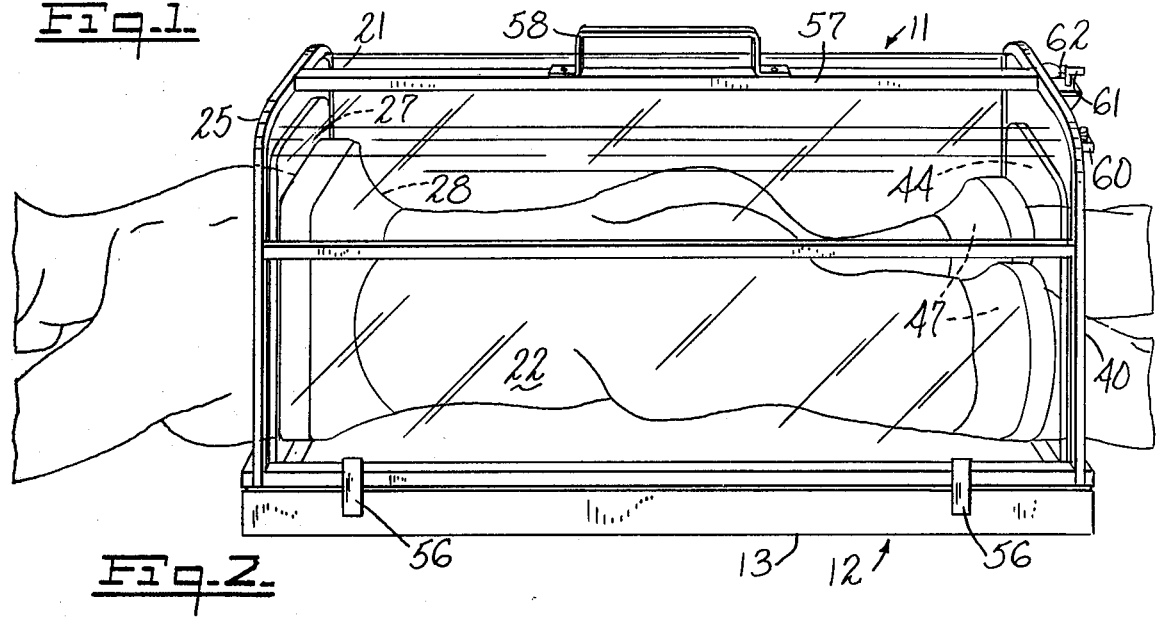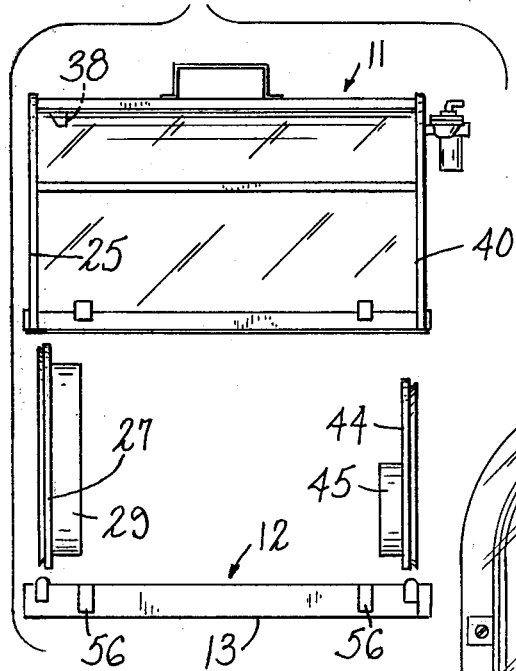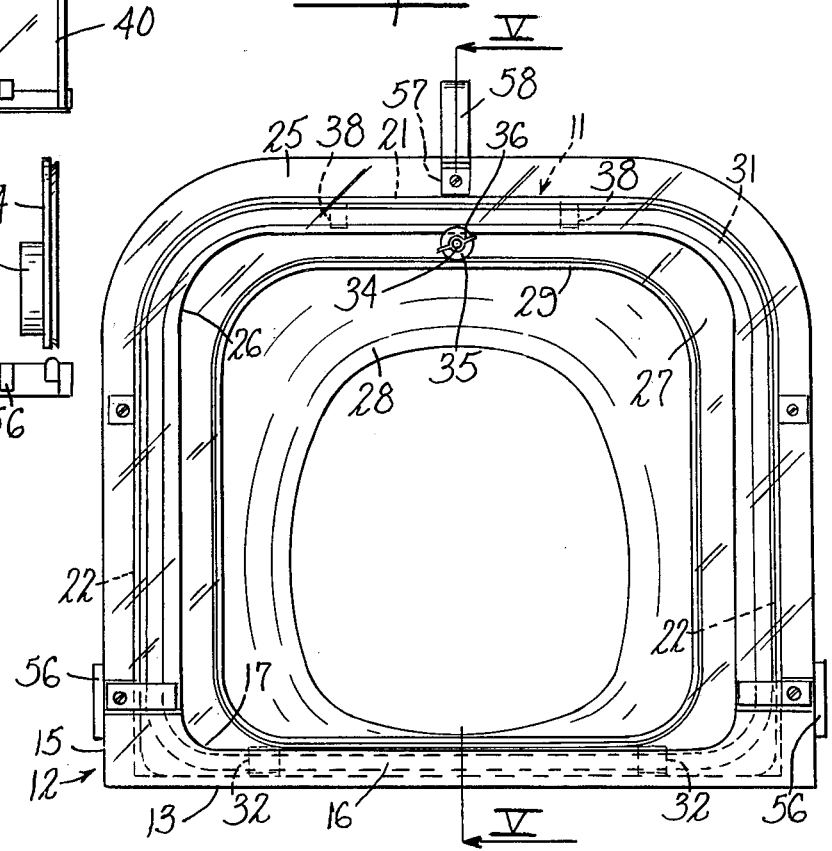

PULSED OXYGEN CHAMBER

This invention relates to a controlled pressure oxygen treatment system which includes a chamber adapted to receive and enclose a portion of a human body including part of the trunk, and a gas (oxygen) supply circuit, with controls, adapted to supply gas to the chamber automatically in pulses of predetermined frequency, duration and pressure. This application is directed to a chamber having capabilities which differ from those of the chamber disclosed in application Ser. No. (Docket 9946) filed of even date herewith.

It is known to use hyperbaric oxygen topically to treat pressure sores, wounds, skin lesions, decubiti and ulcers, chambers for this purpose being shown and described in Fischer U.S. Pat. Nos. 3,744,491, July 10, 1973 and 4,003,371, Jan. 18, 1977. In these chambers the flow of oxygen past the enclosed leg or arm of a patient is continuous, at a low constant pressure of 22 mm. Hg, for example, and is continued for several hours a day (preferably six to eight) over periods which may average several weeks, to aid in the healing of various lesions.

Studies have now revealed that the treatment time for ulcerations and lesions originating from various etiologies can be substantially reduced by resorting to the use of pulsating oxygen treatment, particularly in the present oxygen chamber. Actual trials in a leading hospital have shown a median healing time of 19 days, substantially less than the time required for more conventional treatment.

It is accordingly an object of the present invention to provide a treatment chamber for a portion of a human body specially adapted for use with a pulsed oxygen supply. Suitable oxygen supply circuits are disclosed in Fischer application Ser. No. 858,960 and Ser. No. 052,488.

It is another object of the invention to provide such a chamber which is designed to use the hospital oxygen supply, to which it can be connected and from which it can be removed in seconds.

It is a further object of the invention to provide a chamber which is of simple construction, sturdy and easily cold-sterilize.

It is another object of the invention to provide certain improvements in the form, construction and arrangement of the several parts whereby the above-named and other objects of the invention can readily be achieved.

The invention accordingly comprises the features of construction, combination of elements and arrangement of parts which will be exemplified in the construction hereinafter set forth, and the scope of the invention will be indicated in the claims.

A practical embodiment of the invention is shown in the accompanying drawings wherein:

FIG. 1 represents a somewhat diagrammatic perspective view of the chamber with patient therein;

FIG. 2 represents an exploded side elevation of the chamber;

FIG. 3 represents an elevation of the upper body end of the chamber;

Figure 4:
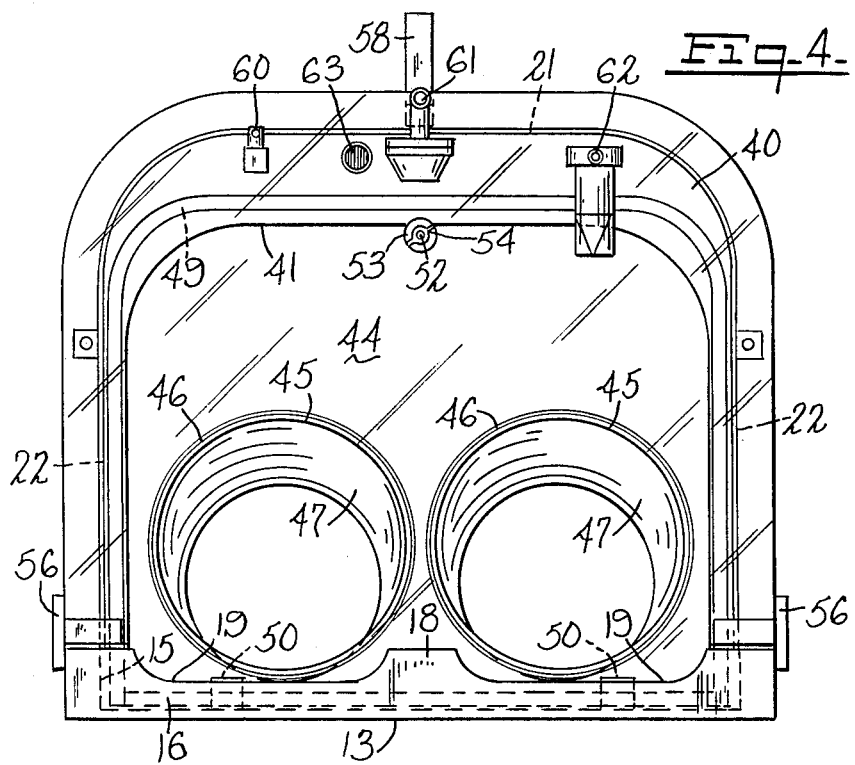
FIG. 4 represents an elevation of the leg end of the chamber.

Referring to the drawings, the oxygen chamber itself comprises upper and lower portions 11, 12, the lower portion 12 including a flat bottom tray 13 having a peripheral flange 14 and a corresponding vertical wall comprising straight side wall portions 15, a body end wall portion 16 cut away to form a wide flat recess 17 (FIG. 3) and a leg end wall portion 18, cut away each side of the center to form two wide flat recesses 19 (FIG. 4). The upper portion 11 of the chamber has a main wall constituted by a flat top portion 21 and vertical side portions 22. The bottom edges of side portions 22 are provided with gaskets (not shown) which seal tightly on the wall portion 15. The body end of the portion 11 is finished by an arcuate flat wall 25, the inner periphery of which, 26, defines, with the wide recess 17, a generally square opening into which is fitted the frame-body sleeve assembly 27-28. This assembly includes the flat wall 27 which frames a generally square opening (with rounded corners) and a flange 29 which projects inwardly from the periphery of the opening and serves as a support for the sleeve 28. The sleeve is of a flexible somewhat elastic material such as surgical grade latex sheeting, somewhat tapered, with its larger, beaded end adapted to fit snugly on the flange 29 where it may be retained by an elastic band 30. Its smaller end is sized to fit snugly around the patient's body in a zone at or above the waist (FIG. 1) and a sufficiently accurate fit can be assured by the provision of sleeves in a range of sizes, up to the capacity of the apparatus.

Figure 5:
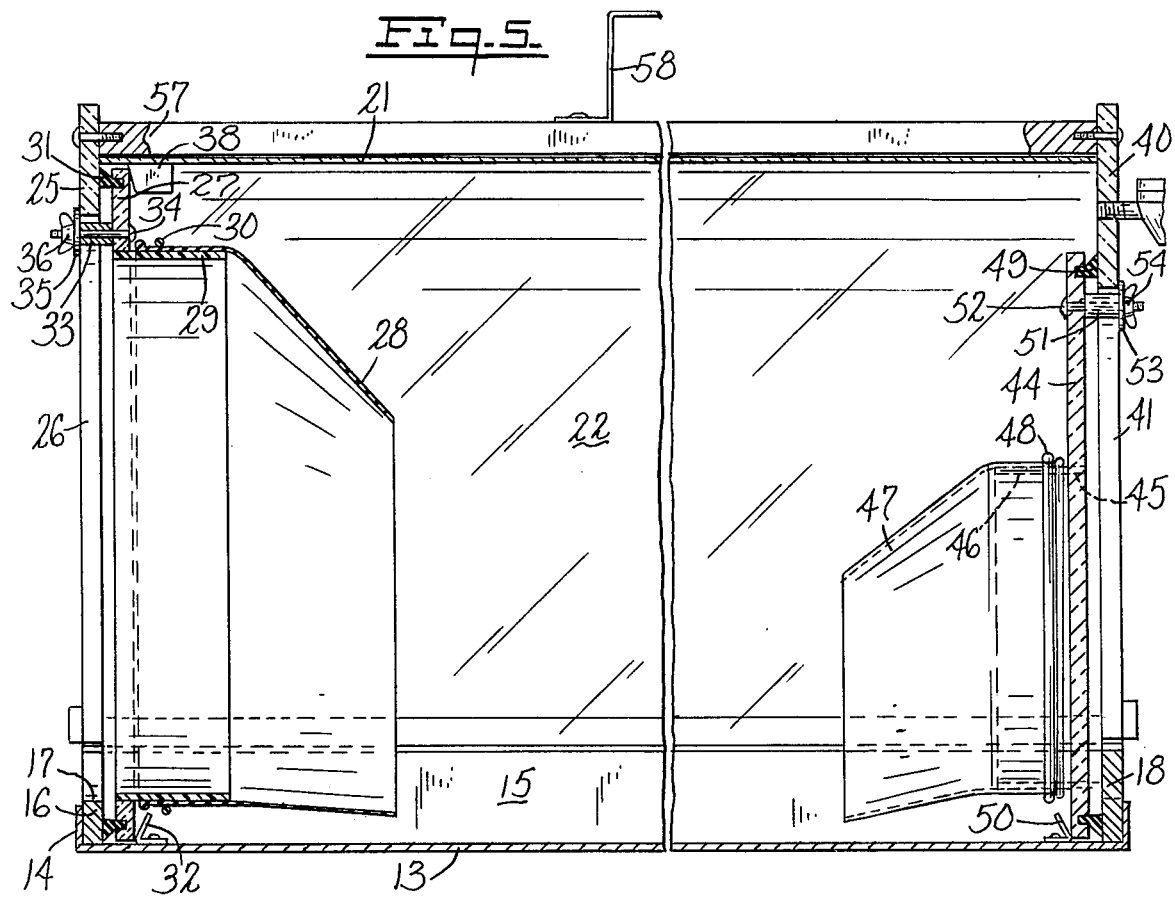
FIG. 5 represents a longitudinal medial vertical section on the line V—V of FIG. 3.

Adjacent the periphery of the wall 27, on its outer face, there is mounted a gasket 31 (FIG. 5), trapeziform in cross-section and adapted to seal against the inner surfaces of the walls 16 and 25. On the floor of the tray 13 are located two or more slanting guides 32 in positions to be engaged by the lower edge of the wall 27 and to wedge it toward the inner surface of wall 16. The wall 27 is provided with a post 33 near the middle of its upper edge, the post housing a bolt 34 on the end of which are a washer 35 and a wing nut 36, the washer having a large enough diameter to overlap the adjacent edge 26 of the wall 25 when the apparatus is assembled, as shown in FIG. 5. Tightening of the wing nut serves to press the gasket 31 sealingly against the adjacent wall surfaces. Firm seating of the gasket is also facilitated by the provision of guide blocks 38 mounted on the top wall 21 and having slanting front sides adapted to wedge the upper edge of the wall 27 toward wall 25.

The structural features at the leg of the chamber are generally similar to those just described, at the body end. The end of the upper portion 11 is finished by the arch-shaped flat wall 40, the inner periphery of which, 41, defines, with the recesses 19 in the upper surface of wall 18, a generally rectangular opening with rounded corners, into which is fitted the frame-leg sleeve assembly. This assembly includes the flat wall 44, the lower portion of which is provided with round openings 45, each provided with an inwardly projecting annular flange 46 to serve as supports for the leg sleeves 47. The leg sleeves are like the body sleeve 28, but provided in a range of smaller sizes, and are retained on the flanges 46 by elastic bands 48.

The wall member 44 has a gasket 49 mounted on its outer face and extending around the entire periphery, like the gasket 31, in a position to be pressed sealingly against the inner surfaces of the walls 40 and 18. On the floor of the tray 13 are located two or more slanting guides 50 (like guides 32) in positions to be engaged by the lower edge of the wall 44 and to wedge it toward the wall 18. Near the middle of its upper edge the wall 44 is provided with a post 51 which houses a bolt 52 on which are a washer 53 and a wing nut 54, so located that the washer will overlap the edge 41 of the wall 40, as shown in FIG. 5. When the frame-leg sleeve assembly is seated with the bottom of wall 44 wedged by guides 50 and washer 53 engaged with wall 40, the tightening of wing nut 54 sets the gasket 49 tightly against the adjacent wall surfaces.

The upper and lower chamber portions 11 and 12 are firmly clamped together by means of toggle-type latches 56, the details of which are conventional and not shown. A rod 57 extends across the top of the upper portion, connecting its ends, and a handle 58 fastened to the rod facilitates lifting of the upper portion or of the entire chamber, if unoccupied.

In use, for the treatment of a lesion on an area of the body between the thighs and waist, for instance, a protective temporary dressing is applied, the frame-body sleeve assembly 27–28 is fitted carefully onto the patient's body (from the feet upward), the frame-leg sleeve assembly is fitted on the patient's legs (thighs) with the free edges of the sleeves 47 extending upward toward the body, as shown in FIG. 1, and the patient is lifted to permit placement of the lower chamber portion 12 under the patient with the frame walls 27 and 44 (properly spaced) engaging the respective guides 32 and 50. The temporary dressing being removed, the upper chamber portion 11 is lowered carefully into place and latched, and the final sealing closure is effected by means of the respective washers and thumb screws, as described above. Disassembly is effected, in general, by reversal of the steps just described.

The adaptability of this chamber for use with the pulsed oxygen supply described in the Fischer application cited above is indicated by the provision, in the upper part of the end wall 40, of gas connection fittings 60, 61 and 62. An overpressure relief vent is shown at 63.

The sleeves are disposable with an anticipated life of two to three days after which time they should be discarded and replaced. Soiled or damaged sleeves should be immediately discarded. To avoid the possibility of cross contamination, the end frames should be used only on a single patient during an entire course of treatment, otherwise sterilization is required.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawing shall be interpreted as illustrative and not in a limiting sense.

What I claim is:

1. A closable chamber for use in gas treatment of areas on a human body between the knees and shoulders, the chamber having a body end and a leg end, comprising separable lower and upper portions and end closure assemblies, the lower portion including a flat tray with body end and leg end walls, the upper portion including body end and leg end walls, said upper portion end walls defining, with the lower portion end walls, an opening at the body end adapted to accommodate the trunk of a human body and an opening at the leg end adapted to accommodate the legs of a human body, the body end closure assembly including a first frame adapted to surround a human body and a sleeve mounted on the first frame and adapted to fit sealingly against a human body in the chamber, the leg end closure assembly including a second frame adapted to surround both legs of a human body, the second frame being provided with sleeve means mounted in the frame and adapted to fit sealingly against said legs.

2. A closable chamber according to claim 1 wherein said first frame is provided with a gasket adapted to rest sealingly against the inner surfaces of the upper and lower body end walls and said second frame is provided with a gasket adapted to rest sealingly against the inner surfaces of the upper and lower leg end walls.

3. A closable chamber according to claim 2 which includes means for holding each of said frames in gasket-compressing positions.

4. A closable chamber according to claim 3 wherein said holding means includes guides on the lower portion engageable by the respective frames and clamping means between the frames and the upper portion.

5. A closable chamber according to claim 4 wherein the guides are slanted to wedge the frames toward the walls and the clamping means is screw threaded.

6. A closable chamber according to claim 1 wherein the second frame has a wall portion which is provided with two openings, each sized to receive freely a human leg and each opening being provided with a tapering annular sleeve adapted to fit sealingly against said legs.

7. A closable chamber according to claim 6 wherein each opening is provided with an inwardly projecting flange and each sleeve is mounted on a respective flange.

* * * * *